United States Patent [19]

Pasarela et al.

[11] Patent Number: 4,871,388
[45] Date of Patent: Oct. 3, 1989

[54] HERBICIDAL LIQUID CONCENTRATE COMPOSITIONS

[75] Inventors: Nunzio R. Pasarela, Brooksville, Fla.; William S. Steller, Fairless Hills, Pa.

[73] Assignee: American Cyanamid Company, Stamford, Conn.

[21] Appl. No.: 60,955

[22] Filed: Jun. 15, 1987

Related U.S. Application Data

[63] Continuation of Ser. No. 829,640, Feb. 14, 1986, abandoned.

[51] Int. Cl.$^4$ ............................................. A01N 25/25
[52] U.S. Cl. .................................. 71/92; 71/DIG. 7; 71/82
[58] Field of Search ...................... 71/92, DIG. 1, 82

[56] References Cited

PUBLICATIONS

Adalla. Chem. Abst. vol. 93, 90069(b), vol. 93 (1980).

Primary Examiner—Catherine L. Mills
Attorney, Agent, or Firm—John W. Hogan, Jr.

[57] ABSTRACT

The present invention relates to liquid concentrate compositions of herbicidal imidazolinyl benzoic acid esters and a method for their preparation.

5 Claims, No Drawings

HERBICIDAL LIQUID CONCENTRATE COMPOSITIONS

This application is a continuation of application Ser. No. 829,640, filed Feb. 14, 1986.

BACKGROUND

Herbicidal imidazolinyl benzoic acids, esters, and salts and their use are described in U.S. Pat. Nos. 4,188,487, 4,297,128 and 4,554,013.

These substituted benzoic acids, esters and salts which are represented by Formula I.

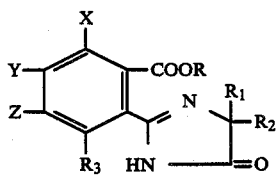

where R is hydrogen;
$C_1$-$C_{12}$ alkyl optionally substituted with one of the following groups: $C_1$-$C_4$ alkoxy, halogen, hydroxyl, $C_3$-$C_6$ cycloalkyl, benzyloxy, furyl, phenyl, halophenyl, $C_1$-$C_4$ alkylphenyl, $C_1$-$C_3$ alkoxycarbonyl, cyano or tri($C_1$-$C_3$) alkylammonium;
$C_3$-$C_{12}$ alkenyl optionally substituted with one of the following groups: $C_1$-$C_3$ alkoxy phenyl, halogen, or $C_1$-$C_3$ alkoxycarbonyl or with two $C_1$-$C_4$ alkoxy groups or two halogen atoms;
$C_3$-$C_6$ cycloalkyl optionally substituted with one or two $C_1$-$C_3$ alkyl groups;
$C_3$-$C_{10}$ alkynyl; or, a cation;
$R_1$ and $R_2$ each represent $C_1$-$C_3$ alkyl or cyclopropyl, with the proviso that the sum of the number of carbon atoms in $R_1$ and $R_2$ is 2 to 5; and when $R_1$ and $R_2$ are taken together with the carbon to which they are attached, they may form a $C_3$-$C_6$ cycloalkyl ring optionally substituted with methyl;
X is hydrogen, halogen or methyl;
Y and Z are each hydrogen, halogen, $C_1$-$C_6$ alkyl, $C_1$-$C_4$ hydroxyalkyl, $C_1$-$C_6$ alkoxy, $C_1$-$C_4$ alkylthio, phenoxy, $C_1$-$C_4$ haloalkyl, $OCF_2CHF_2$, $OCF_3$, $OCHF_2$, nitro, cyano, $C_1$-$C_4$ alkylsulfonyl, $NR_4R_5$, $C_3$-$C_8$ straight or branched alkenyloxy optionally substituted with one to three halogens, $C_3$-$C_8$ straight or branched alkynyloxy optionally substituted with one to three halogens, or phenyl optionally substituted with one or two $C_1$-$C_4$ alkyl, $C_1$-$C_4$ alkoxy or halogen or combinations of any two of these groups;
$R_3$ is hydrogen, halogen, $C_1$-$C_4$ alkyl, $C_1$-$C_4$ alkylthio, $C_1$-$C_4$ alkoxy, $CF_3$, $NO_2$, $OCF_3$, $OCHF_2$ or $OCF_2CHF_2$;
$R_4$ is hydrogen or $C_1$-$C_4$ alkyl;
$R_5$ is $C_1$-$C_4$ alkyl; And, when taken together, Y and Z may form a ring in which YZ is represented by (1) the structure: $-(CH_2)n-$, where n is an integer of 2, 3 or 4; or (2) by the structure:

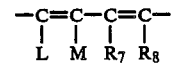

where L, M, $R_7$ and $R_8$ each represent hydrogen, halogen, $C_1$-$C_4$ alkyl or $C_1$-$C_3$ alkoxy, or the isomeric mixture thereof are active herbicidal agents effective for controlling aquatic plants and a wide variety of annual and perennial plant species including field bind weed, wild oats, quackgrass and, with some compounds, velvetleaf and/or nutsedge.

The herbicidal agents are effective for controlling the plants when applied to the foliage thereof or to soil or water containing seeds or other propagating organs of said plants such as tubers, rhizomes or stolons, at rates of from about 0.125 to 10.0 kg/ha.

Many of these compounds are well tolerated by a variety of crops including graminaceous crops and, legumes and sugar beets. They can be applied to the foliage of undesirable plant species or to soil containing seeds or other propagating organs thereof to control the same, and may be used in the form of liquid sprays or solid formulations for such applications.

When the compounds are water soluble such as the free acids and salts thereof, they may be simply dissolved in water and applied as such. These acids and salts may also be formulated as wettable powders, flowable concentrates, emulsifiable concentrates, granular formulations and the like.

However, when R is other than hydrogen or a cation, the resulting Formula I benzoic acid esters exhibit limited solubility, both in water and water miscible solvents. This limited solubility of these esters has heretofore restricted the concentrations obtainable and hence their use in aqueous spray applications.

It is an object of this invention to provide liquid concentrate compositions of imidazolinyl benzoic acid esters in water miscible solvents which are physically stable, contain relatively high concentrations of the imidazolinyl benzoic acid esters, and are suitable for application by dilution in water.

SUMMARY

The invention relates to liquid concentrate compositions comprising on a weight basis 1% to 45% of a herbicidal imidazolinyl benzoic acid ester, 0.2 to 1 molar equivalent of certain polybasic acids and sulfonic acids, 0.0% to 99% of an alcohol corresponding to R in the Formula I compound, 0.0% to 20% of a non-ionic surfactant, and 0% to 99% of a water miscible organic solvent. Water miscible organic solvents preferred for use in the compositions of this invention include alcohols, ketones, dimethylformamide, dimethylsulfoxide, N-methylpyrrolidone, and the like.

It has been found that, herbicidal imidazolinyl benzoic acid esters such as a recently commercialized herbicide which is an isomeric mixture of 6-(5-isopropyl-5-methyl-4-oxo-2-imidazolin-2-yl)-m-toluic acid, methyl ester and 2-(5-isopropyl-5-methyl-4-oxo-2-imidazolin-2-yl-p-toluic acid, methyl ester have limited solubility (15% or less by weight) at room temperature in many of the solvents listed in Table I below.

When solutions of said ester(s) in those solvents with >15% solubility are diluted in water to normal agricultural tank-mix rates (1:9-1:99), unsprayable precipitates are formed.

TABLE I

Solubility of the Isomeric Mixture of
6-(5-isopropyl-5-methyl-4-oxo-2-imidazolin-2-yl)-m-toluic acid, methyl ester and
2-(5-isopropyl-5-methyl-4-oxo-2-imidazolin-2-yl)-p-toluic acid, methyl ester
at Room Temperature in Various Solvents
% Solubility by Weight

| >15% | 10%-15% | 5%-10% | 5% |
|---|---|---|---|
| Methanol | Tetrahydrofurfuryl alcohol | Acetonitrile | Amyl acetate |
| N—methylpyrrolidone | Diacetone alcohol | Butyrolactone | Anisole |
| Dimethylformamide | Methyl benzoate/methyl- p-toluate | Glycerol formal | Aromatic 150 |
| Chloroform | Cyclohexanone | Panasol AN-2 | Diethyl succinate |
| Dimethyl sulfoxide | Isophorone | Pine Oil | Triethanolamine |
| 1-Formylpiperidine | Cyclohexanone | Methyl isobutyl ketone | Oleic acid |
| 1-propanol | 2-Ethylhexanol | 3-NOX | Methyl oleate |
| Methyl cellosolve | | Supersol BP | Penn Drake Oil (Kerosene) |
| Amyl alcohol (mixed) | | 1,1,1-Trichloroethane | Propylene glycol |
| | | | Tenneco 500/1000 |
| | | | Xylene |

It has also been found that the solubility of these compounds may be increased by the addition of 0.2 to 1 molar equivalent of certain acids. Additionally, it has been found that in solvents, in which this isomeric mixture has greater than 20% by weight solubility that the dissolution characteristics of the resulting concentrate are not satisfactory without the addition of 0.2 to 1.0 molar equivalent of acids such as sulfuric or sulfonic acids such as p-toluenesulfonic acid, as illustrated in Table II below which shows the effects of the addition of various acids, having differing pKa's on the dissolution of a 43% by weight liquid concentrate composition of the isomeric mixture of 6-(5-isopropyl-5-methyl-4-oxo-2-imidazolin-2-yl)-m-toluic acid, methyl ester and 2-(5-isopropyl-5-methyl-4-oxo-2-imidazolin-2-yl-p-toluic acid, methyl ester in 56.9% by weight of N-methylpyrrolidone.

TABLE II

Dissolution Properties of 7.5 g of Liquid Concentrate Compositions[1] Utilizing 1 Molar Equivalent of Different Acids

| Acid | Initial Solubility | Dissolution in 100 mL $H_2O$ |
|---|---|---|
| Sulfuric | soluble | clear 24 hrs |
| Phosphoric | soluble | floc. within 24 hrs |
| Hydrochloric | soluble cloudy | floc. initially |
| Hydrochloric anhydrous | soluble cloudy | floc. initially |
| p-toluene- sulfonic | soluble when heated | clear 24 hrs |
| acetic | soluble cloudy | floc. initially |
| citric | insoluble | floc. initially |
| oleic | soluble cloudy | floc. initially |
| boric | soluble when warmed | floc. initially |
| gluconic | insoluble | floc. initially |
| benzoic | soluble when warmed | floc. initially |
| thioglycolic | soluble | floc. initially |
| formic | soluble cloudy | floc. initially |
| dodecylbenzene- sulfonic | soluble when warmed | floc. initially |
| stearic | soluble when warmed | floc. initially |
| p-aminobenzoic | insoluble | floc. initially |
| tannic | insoluble | floc. initially |
| salicylic | soluble | floc. initially |

[1]43.06% by weight of the isomeric mixture of 6-(5-isopropyl-5-methyl-4-oxo-2-imidazolin-2-yl)-m-toluic acid, methyl ester and 2-(5-isopropyl-5-methyl-4-oxo-2-imidazolin-2-yl-p-toluic acid, methyl ester. 56.94% by weight N—methylpyrrolidone Further it has been found that when alcohols such as tetrahydrofurfuryl alcohol methyl cellosolve, or 2-alkoxyethanols and the like are employed as solvents in liquid concentrate compositions of imidazolinyl benzoic acid esters, that the incorporation of another second appropriate alcohol which corresponds to the R group in the Formula I imidazolinyl benzoic acid ester in conjunction with the incorporation of 0.5 to 1 molar equivalents of an acid, greatly enhances the integrity of the ester functionallity R, both at elevated temperatures and ambient temperatures for extended periods of time. Preferred weight ratios of the alcohol ROH to co-solvent alcohol are in the range of 1.0:1.0 to 3.0:2.0 for use in the liquid concentrate compositions of this invention, in conjunction with molar ratios of imidazolinyl benzoic acid ester to acid in the range of 0.5:1.0.

Alternatively the alcohol corresponding to R in the Formula I compounds, or a non-hydroxylic water miscible solvent may be employed alone, in conjunction with an acid as described above. The liquid concentrate compositions of the invention may optionally contain 0% to 20% by weight of a non-ionic surfactant or foliar wetting agent.

Liquid concentrate compositions of the invention may readily be prepared by adding an acid to a stirred homogeneous slurry of the imidazolinyl benzoic acid ester in the appropriate solvent or mixture of solvents. The resulting mixture is stirred until a solution is obtained, and a non-ionic surfactant may then be added to the stirred solution to act as a foliar wetting agent if desired. The resulting solution may then be clarified by filtration to give a chemically stable liquid concentrate compositions of imidazolinyl benzoic acid esters which have physically acceptable properties both in concentrate form and upon dilution in water.

The invention is further illustrated by the following non-limiting examples.

EXAMPLE 1

Preparation of Herbicidal Liquid Concentrate Compositions of Imidazolinyl Benzoic Acid Ester To a beaker containing 3.1 g of methanol and 2.5 g of tetrahydrofurfuryl alcohol is added 3.1 g of an isomeric mixture of 6-(5-isopropyl-5-methyl-4-oxo-2-imidazolin-2-yl)-m-toluic acid, methyl ester and 2-(5-isopropyl-5-methyl-4-oxo-2-imidazolin-2-yl)-p-toluic acid, methyl ester (94.2% assay, 0.010 mol). While stirring, the mixture 0.5 g of concentrated (96%) $H_2SO_4$ (0.00489 mole) is added. Stirring is continued until the solid dissolves, and then 0.8 g of an ethoxylated linear alcohol is added and the mixture stirred until homogeneous. Utilizing the above procedure yields the liquid concentrate compositions listed in Table III below.

These compositions are stored at 45° C. for three months and the percent recovery of herbicide determined. The results of these stability tests which are summarized in Table III demonstrate the improved stability of the compositions of the invention containing an alcohol corresponding to R and 0.5 to 1.0 molar equivalents of polybasic acid.

TABLE III

Percent Recovery of Herbicide From Various Compositions After Three Months At 45° C.

| Solvent System | $H_3PO_4$ 1 mol | $H_2SO_4$ 1 mol | $H_2SO_4$ 0.5 mol |
|---|---|---|---|
| methyl cellosolve | | | 48 |
| diacetone alcohol | | | 66 |
| 2-ethoxyethanol | | | 48 |
| 2-methoxyethanol | | | 49 |
| butyl cellsolve | | | 42 |
| tetrahydrofurfuryl alcohol (THFA) | 86 | | 55 |
| methanol | | | 100 |
| N—methyl-2-pyrrolidone | | | 96 |
| 3 methanol/2 THFA | 95 | | |
| 3 methanol/1 THFA | | | 97 |
| 1 methanol/1 THFA | | 95 | 93 |
| 3 methanol/2 THFA | | | 96 |
| 1 methanol/8 THFA | 87 | | |
| 1 methanol/9 THFA | | | 70 |
| 1 methanol/4 THFA | | | 75 |
| 1 methanol/4 diacetone alcohol | | | 80 |
| 1 methanol/9 methyl cellosolve | | | 65 |
| 1 methanol/9 diacetone alcohol | | | 74 |
| 1 methanol/4 methyl cellosolve | | | 75 |
| 1 methanol/4 butyrolactone | | | 82 |
| 1 methanol/3 butyrolactone | | | 85 |

TABLE III-continued

Percent Recovery of Herbicide From Various Compositions After Three Months At 45° C.

| Solvent System | $H_3PO_4$ 1 mol | $H_2SO_4$ 1 mol | $H_2SO_4$ 0.5 mol |
|---|---|---|---|
| 1 methanol/16 methyl cellosolve | | | 54 |
| 1 methanol/48 methyl cellosolve | | | 48 |

What is claimed is:

1. A liquid concentrate composition comprising on a weight basis 1% to 45% of a herbicidal imidazolinyl benzoic acid ester; 0.2 to 1 molar equivalents of sulfuric acid or p-toluene sulfonic acid; 0.0% to 99% of a $C_1$-$C_4$ alkyl alcohol; 0.0% to 20% of a non-ionic surfactant; and 0% to 99% of a water miscible organic solvent; wherein said herbicidal benzoic acid ester is an isomeric mixture iof 6-(5-isopropyl-5-methyl-4-oxo-2-imidazolin-2-yl)-m-toluic acid, methyl ester and 2-(5-isopropyl-5-methyl-4-oxo-2-imidazolin-2-yl)-p-toluic acid, methyl ester, and said water miscible organic solvent is N-methylpyrrolidone, dimethylsulfoxide, dimethylformamide or a mixture of tetrahydrofurfuryl alcohol, diacetone alcohol or butyrolactone in combination with the $C_1$-$C_4$ alkyl alcohol.

2. The composition according to claim 1 wherein the acid is sufuric acid and the solvent is N-methylpyrrolidone.

3. The composition according to claim 1 wherein the solvent is a mixture of a $C_1$-$C_4$ alkyl alcohol with tetrahydrofurfuryl alcohol in a weight ratio in the range of 1:1 to 3:2.

4. The composition according to claim 3 wherein the $C_1$-$C_4$ alkyl alcohol is methanol.

5. The composition according to claim 3 wherein the mole ratio of the sulfuric acid or p-toluene sulfonic acid to herbicidal benzoic acid ester is in the range of 0.5 to 1.0.

* * * * *